United States Patent
Italiaie

(10) Patent No.: US 11,304,731 B2
(45) Date of Patent: Apr. 19, 2022

(54) ANTI-SPLAY HEAD AND SET SCREW FOR SPINAL FIXATION

(71) Applicant: Warsaw Orthopedic, Inc., Warsaw, IN (US)

(72) Inventor: Christel Italiaie, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 167 days.

(21) Appl. No.: 16/723,381

(22) Filed: Dec. 20, 2019

(65) Prior Publication Data

US 2021/0186568 A1    Jun. 24, 2021

(51) Int. Cl.
| | | |
|---|---|---|
| A61B 17/70 | (2006.01) |
| A61B 17/88 | (2006.01) |
| A61B 17/86 | (2006.01) |
| A61B 34/30 | (2016.01) |
| A61B 17/00 | (2006.01) |

(52) U.S. Cl.
CPC ...... *A61B 17/7032* (2013.01); *A61B 17/8685* (2013.01); *A61B 17/7082* (2013.01); *A61B 34/30* (2016.02); *A61B 2017/00526* (2013.01)

(58) Field of Classification Search
CPC ............ A61B 17/7032; A61B 17/8685; A61B 17/7082; A61B 34/30; A61B 2017/00526
USPC ....... 606/266, 267, 268, 269, 270, 272, 273, 606/274, 275, 305, 308, 319
See application file for complete search history.

(56) References Cited

U.S. PATENT DOCUMENTS

| | | | |
|---|---|---|---|
| 8,465,528 B2 * | 6/2013 | Schumacher | ...... A61B 17/7037 606/273 |
| 10,383,675 B1 | 8/2019 | Cummins et al. | |
| 10,548,639 B2 * | 2/2020 | Blakemore | .......... A61B 17/701 |
| 2004/0260284 A1 | 12/2004 | Parker | |
| 2007/0270813 A1 | 11/2007 | Garamszegi | |

(Continued)

FOREIGN PATENT DOCUMENTS

WO    2004032726 A2    4/2004

OTHER PUBLICATIONS

European Patent Office, 80298 Munich, Germany, Extended European Search Report, Application No. 20208618.7, dated May 21, 2021.

(Continued)

*Primary Examiner* — Ellen C Hammond
*Assistant Examiner* — David C Comstock
(74) *Attorney, Agent, or Firm* — Sorell Lenna & Schmidt LLP

(57) ABSTRACT

An anti-splaying system having a base, first and second arms, first and second locking channels. Each of the first and second locking channels is formed in a respective one of the arms, from a proximal opening to a proximal bottom at or adjacent a proximal beginning of an inner thread in the arm. The system can instead or also include a set screw having a driving portion, a body portion, external threads extending from the body portion, and an intermediate locking component connected rotatably to the body portion. The intermediate locking component and the channels are configured such that the locking component can, in operation of the system, be moved into a securing position in the locking channels and, when in the secured position, fixes the two arms from splaying away from each other. The technology also includes methods for making the system or components thereof.

20 Claims, 6 Drawing Sheets

(56) References Cited

U.S. PATENT DOCUMENTS

| | | |
|---|---|---|
| 2008/0234757 A1 | 9/2008 | Jacofsky et al. |
| 2014/0228890 A1* | 8/2014 | Raju ................ A61B 17/7032 606/270 |
| 2015/0282842 A1* | 10/2015 | Beyar ............... A61B 17/7037 606/273 |
| 2016/0296266 A1 | 10/2016 | Chandanson et al. |
| 2018/0243022 A1 | 8/2018 | Marek et al. |
| 2021/0186565 A1* | 6/2021 | Italiaie ............... A61B 17/7032 |

OTHER PUBLICATIONS

European Patent Office, 80298 Munich Germany, European Search Report, Application No. 151315.5-1 132, Applicant: Warsaw Orthopedic, Inc., dated Jun. 16, 2021.

* cited by examiner

ANTI-SPLAY HEAD AND SET SCREW FOR SPINAL FIXATION

FIELD

The present technology is related generally to spinal fixation systems and processes and, more particularly, to an anti-splay head and set-screw arrangement.

BACKGROUND

Surgical screws and rods are used commonly in surgically correcting spinal abnormalities. Pedicle screw assemblies are used to facilitate placement and attachment of a spinal rod relative to the spine. Such pedicle screw assemblies include at least a bone screw section or anchor and at least one receiver portion attached to the bone screw. The bone screw sections are anchored to the vertebrae in the surgical procedure.

The receiver portions have arms between which portions of the spinal rod is received. The arms are often configured with internal threading corresponding to threading on a set screw. Following screw anchoring in the bone, and placement of the rod between the arms of the receiver, a set screw is threaded between the arms to secure the rod in the receiver.

The receiver portions of typical pedicle screws can be angularly or fixedly positionable with respect to the screw sections to facilitated desired attachment of the spinal rod between vertebrae.

Outward forces on the receiver arms over time following implantation try to splay the arms away from each other. One manner of limiting splay is by receiver and set-screw threads configured, such as with sloping thread faces, such that the set screw holds the arms inward, against the set screw.

Other attempted solutions for splaying include using a cap installable around at least a portion an exterior of the receiver arms, to hold the arms from moving away from each other.

These and other prior efforts to avoid splaying have various shortcomings. Shortcomings include undesirable cost, form factor (e.g., implant size or fit within the patient), and strength over time.

SUMMARY

The systems, process, and techniques of this disclosure relate generally to an anti-splay head and set-screw arrangement.

In one aspect, the present disclosure provides an anti-splaying system. The system includes a receiver having a base, a first arm, a second arm, a first locking channel, and a second locking channel. The first arm and the second arm each extend from the base defining a rod-receiving cavity between the arms. The first and second arms include first and second inner threads formed in respective inner surfaces of the first and second arms. The first locking channel is formed in the inner surface of the first arm and extending from a proximal opening to a proximal bottom at or adjacent a first proximal beginning of the first inner thread. The second locking channel is formed in the inner surface of the second arm and extending from a proximal opening to a proximal bottom at or adjacent a second proximal beginning of the second inner thread.

Further in this aspect, the system includes a set screw having a driving portion, a body portion, external threads extending from the body portion, and an intermediate locking component connected rotatably to the body portion.

The intermediate locking component of the set screw and the locking channels of the receiver are configured such that the locking component can, in operation of the system, be moved into a securing position in the locking channels and, when in the secured position, fixes the two arms from splaying away from each other.

The intermediate locking component is connected rotatably to the body portion intermediate the driving portion and the external threads of the set screw.

The locking component comprises opposing lateral ends sized and shaped corresponding to size and shape of the locking channel, for mating engagement between the locking component and the locking channels.

A first lateral end of the lateral ends comprises opposing shoulders sized and shaped to engage opposing shoulders of a first locking channel of the locking channels The lateral ends include first and second lateral ends, and the connecting component includes first and second arms connecting the first and second lateral ends respectively to the ring.

The locking channel has a depth that is about twice as deep as the locking ends are tall or less.

The locking component includes a ring surrounding a portion of the set screw body. The body has a reduced diameter where the ring surrounds the body.

In another aspect, the system further includes a bone anchor connectable with the receiver, and the spinal rod.

In still another aspect, the technology includes methods of making any of the anti-splaying systems or anti-splay components described above.

Details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
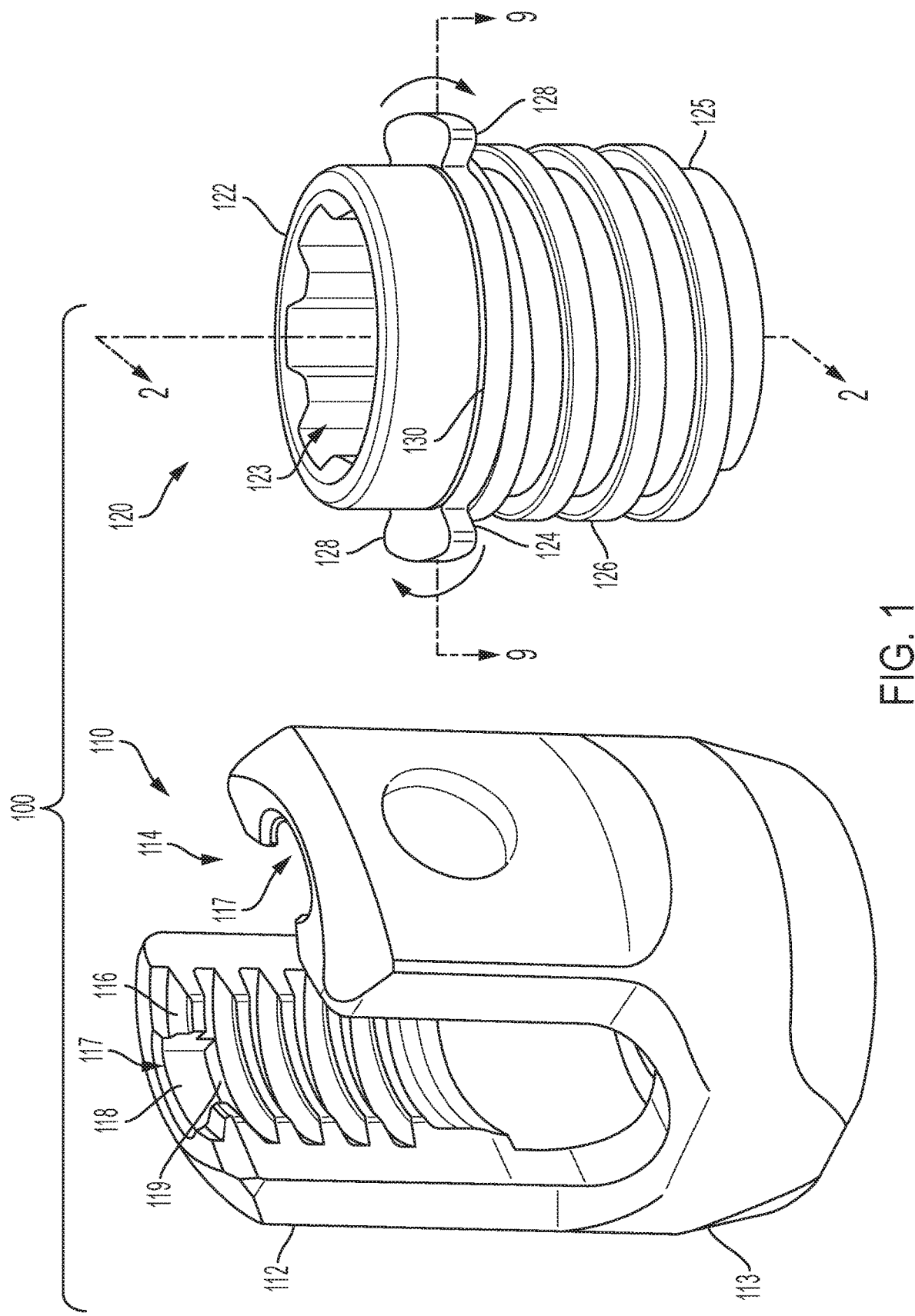
FIG. 1 shows perspective views of an anti-splaying system partially disassembled, the system including an anti-splay receiver and an anti-splay set screw, according to embodiments of the present disclosure.

Turning now to the drawings, and more particularly to the first figure, FIG. 1 shows a perspective view of components of an anti-splay system, indicated generally by reference numeral 100.

The system 100 includes an anti-splay head, or receiver 110, and an anti-splay set screw 120, according to embodiments of the present disclosure.

The receiver 110 has arms 112 extending up, or proximally, from a base 113. The arms 112 define a rod cavity 114 between them, for receiving a spinal-fusion rod. A rod 300 is shown schematically, disposed in the cavity 114, in FIGS. 3 and 8.

The set screw 120 extends from a driving, or proximal, end having a driving portion 122. The driving portion 122 includes a driving port 123. The driving port 123 may be a cavity sized and shaped corresponding to any available set-screw driver (now shown).

The set screw 120 further includes a shaft, or body 125 extending to a distal end of the screw 120. In a contemplated embodiment, the driving portion 122 can be formed integrally or monolithically with or in the body 125 of the set screw 120.

The body 125 has a threaded exterior 126. The threaded surface 126 corresponds in size and shape to a thread 116 of the receiver 110, for being threaded into the receiver.

The set screw 120 further includes a locking component 124. The locking component 124 is connected rotatably to the body 125, as indicated by arrows in FIG. 1.

The locking component 124 is in various embodiments connected to the body 125 intermediate the driving portion 122 and the screw threads 126. The locking component 124 can be referred to in such cases as an intermediate locking component, an intra-screw locking component, or the like.

While the arrows in FIG. 1 indicate a first direction of rotation, the connecting features are in various embodiments configured so that the locking component 124 can rotate in both direction, or in one direction or the other, only.

Figure 2:
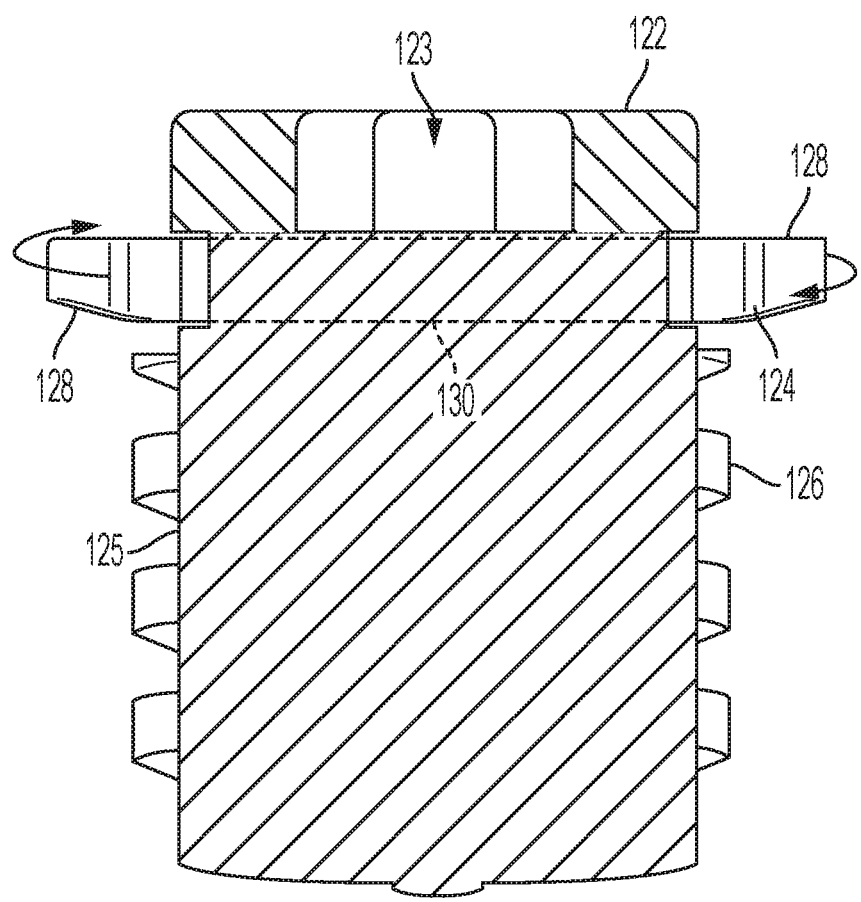
FIG. 2 is a cross section of the anti-splay set screw taken along line F2-F2 of FIG. 1.

The locking component 124 extends between opposing ends 128. The ends 128 of the locking component 124 are connected by a central connector 130. The connector in various embodiments is shaped as a ring 130. The ring 130 surrounds a portion of the body 125 extending up to the driving portion 122, as shown well in FIG. 2. In various embodiments, the body 125 has a reduced diameter to accommodate the ring, as shown in FIG. 2.

The connection in various embodiments includes features facilitating the relative rotation between the ring 130 and the body 125, such as ball-bearings or a medical lubricant.

The ends 128 can extend by arms 127 connecting the ends 128 to the central connecting structure 130, e.g., connecting ring 130.

With further reference to the anti-splay receiver 110, each arm 112 has an internal thread set 116. As shown in FIG. 1, each thread set 116 is interrupted or separated by an anti-splay, or locking, channel 118 at a proximal end of the receiver threads 116. The threads 116 oppose each other across the cavity 114, and can be referred to as opposing threads or thread sections.

Figure 3:
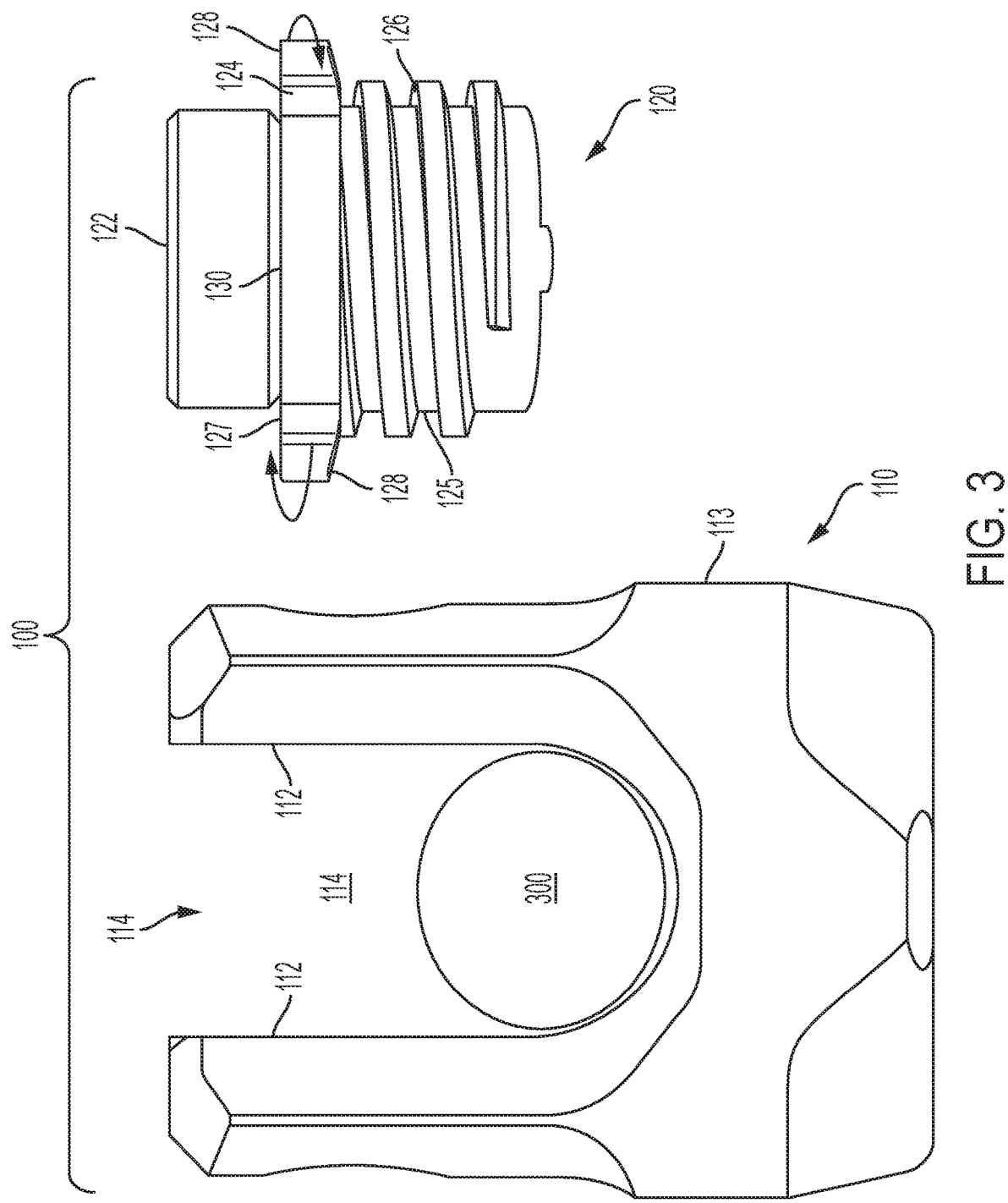
FIG. 3 is a side view of the anti-splaying system of FIG. 1.

Each locking channel 118 extends distally from a proximal opening 117 (referenced in FIG. 1) to a distal stop or bottom. In operation of the system 100, the anti-splay set screw 120 is threaded into the anti-splay receiver 110 until the locking component 124 enters the locking channel 118. The threading can be performed until the locking component 124 engages with the channel stop 119 (FIG. 7) and/or the distal end of the body engages the spinal rod 300 (FIGS. 3 and 8). Engaging the rod is in most embodiments the priority.

The locking channel 118 is sized and shaped, and the anti-splay set screw 120 is sized and shaped, such that the set screw 120 extends distally in being threaded into the receiver 110 until the rod is contacted by the distal end of the rod. At that time, or after a certain small amount of further threading, such as a quarter, half, or full turn of the screw 120, the locking component 124 bottoms out at stop 119 of the channel 118. The system 100 is in some embodiments designed, and the rod sized, such that the locking end 128 enters the channel 118 completely, even if it doesn't bottom out.

The locking channel must be sufficiently deep. If the locking channel 118 is not deep enough, the locking component 124 would bottom out, at the stop 119, before the set screw 120 is able to thread sufficiently into the receiver 110.

In various embodiments, the stop 119 is at or adjacent a top of the corresponding inner thread 116. The stop 119 may be at or adjacent a first, second, or third level of inner threading 116, for instance. In the example of FIG. 1, the channel extends through a single level of inner thread from the top or opening 117, with the stop 119 being generally at start of a second level of inner thread from the top or opening 117. These areas, including the first one or few threads, can be referred to generally as a proximal beginning of the inner thread.

In various embodiments, the channel depth is at least equal to a height of the locking component 124, or a height of the ends 128 of the locking component 124.

In contemplated embodiments, the system 100, or a kit in which the system is provided, includes any of the components referenced. The system or kit can include any suitable components for performing the surgical procedures, including but not limited to implantable components and instruments for effecting the surgery. The system 100 can include, for instance, any of the anti-splay receiver 110, the anti-splay set screw 120, and the rod 300. The system 100 or kit can include the driver referenced, but not shown. And the system 100 or kit can include any number and size of these parts, including multiple anti-splay set screws and receivers 120, 110.

Turning to the second figure, FIG. 2 illustrates a cross section of the set screw 120, taken along line F2-F2 of FIG. 1.

In operation of the system 100 (FIG. 1), the locking component 124 is aligned into the locking channel 118 of the receiver 110, by a surgeon or surgical robot. As the anti-splay set screw 120 is threaded into the receiver 110, by the surgeon or robot turning a driver (or, driving instrument; not shown) against a driving portion 220 of the driving portion 122, the locking component 124 enters the channel 118.

FIG. 3 is a side view of the anti-splay receiver 110 and anti-splay set screw 120 of FIG. 1. Rotatability of the locking component 124 relative to the set-screw body 125 is indicated again by arrow.

FIG. 3 also shows schematically an end view of the rod 300 positioned in the cavity 114 of the receiver 110.

Figure 4:
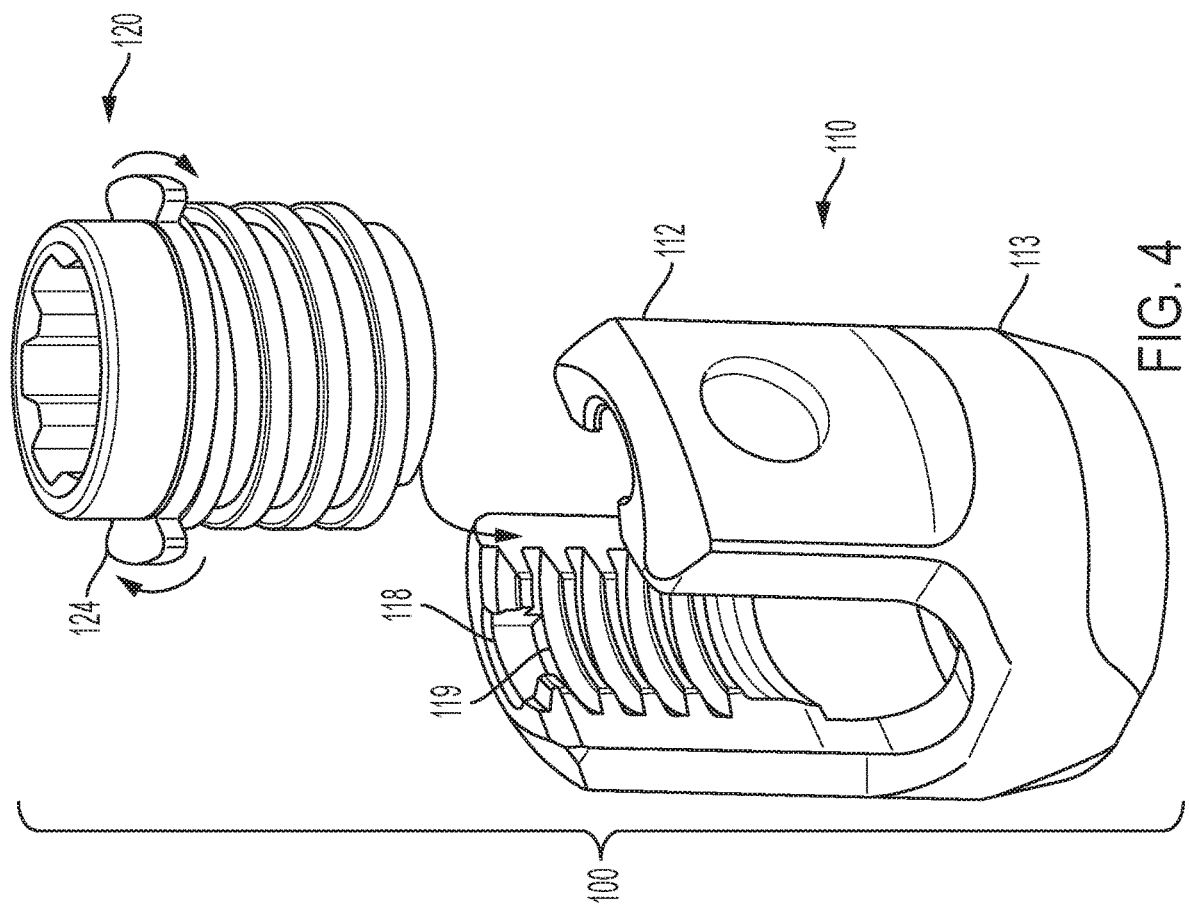
FIG. 4 is a perspective view of the anti-splay set screw being lowered for insertion to the receiver.

FIG. 4 is a perspective view of the anti-splay set screw 120 being positioned for lowering for insertion to the anti-splay receiver 110. The movement is indicated generally by arrow in FIG. 4.

Prior to the movement of FIG. 4, the receiver 110 is secured to a patient vertebra, by a bone screw connected to the receiver 110. The bone screw (not shown) can be any conventional or available type. The receiver 110 can be configured for top-loading or bottom-loading of the bone screw into the receiver 110. The receiver 110 may in such ways be connected or connectable to the bone anchor readily—e.g., easily in the usual course of a surgery.

The anti-splay receiver 110 and anti-splay bone screw 120 can be further configured to allow desired relative motion, such as uniaxial or multiaxial motion. In some embodiments, the bone screw and the receiver 110 are fixed together, either by being formed integrally or monolithically, or by being fixedly connected to each other.

In operation of the anti-splaying system 100, before and/or as the set-screw 120 is moved toward the receiver 110, care is taken such that the locking ends 128 of the locking component 124 are aligned with the anti-splay channels 118 of the arms 112 of the receiver 110.

The anti-splay channels 118 receive ends 128 of the locking component 124. In various embodiments the locking component 124 is sized such that the ends extend further laterally than a maximum diameter of the screw body 125, and in some cases farther than a maximum diameter than the thread 126, as shown in the figures, and best seen in FIG. 2.

Figure 5:
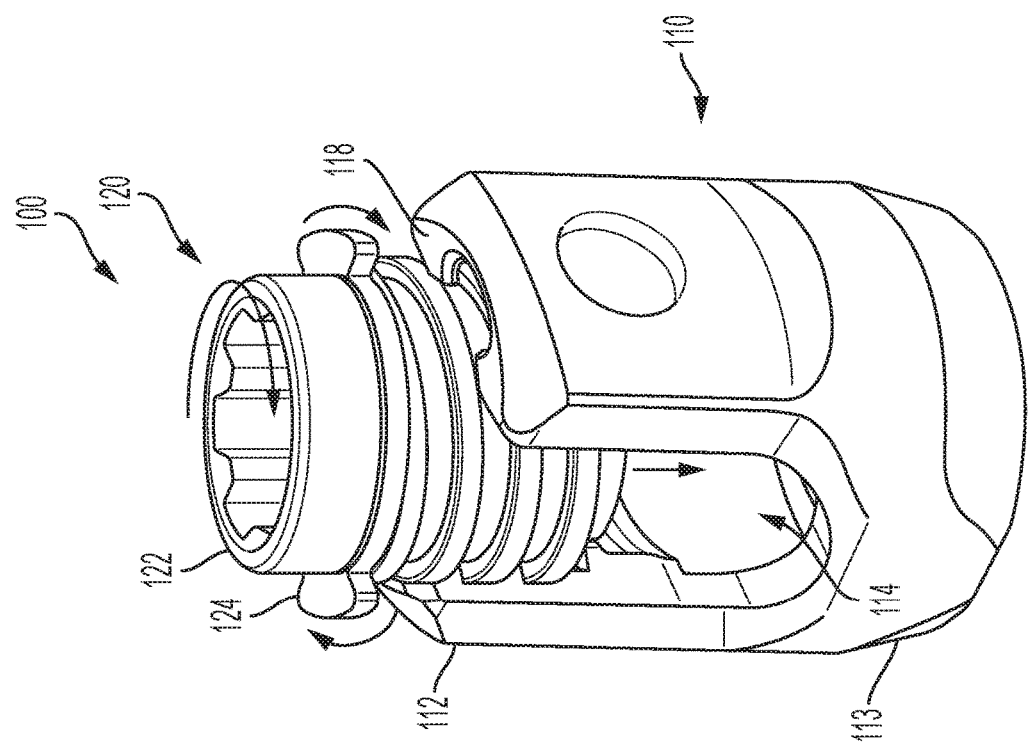
FIG. 5 is the perspective view of FIG. 4 with the anti-splay set screw being threaded toward a final position within the anti-splay receiver.

FIG. 5 shows the anti-splay set screw 120 having been threaded to a final position within the anti-splay receiver 110. In this position, the locking component 124 would seat against the rod 300, which is shown in FIGS. 3 and 8. Motion of threading, transitioning the set screw 120 toward the final position, is indicated by arrow in FIG. 5.

Figure 6:
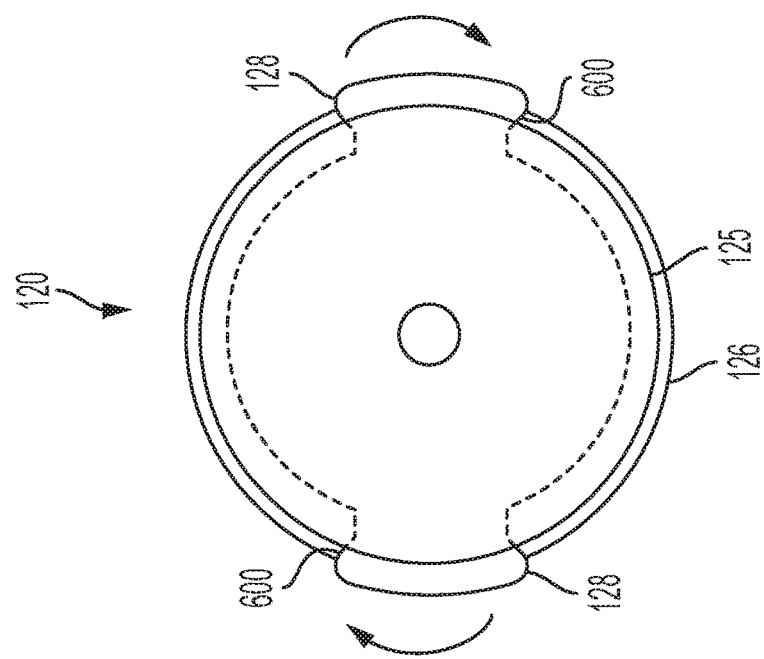
FIG. 6 is a bottom view of the anti-splay set screw.
Figure 9:
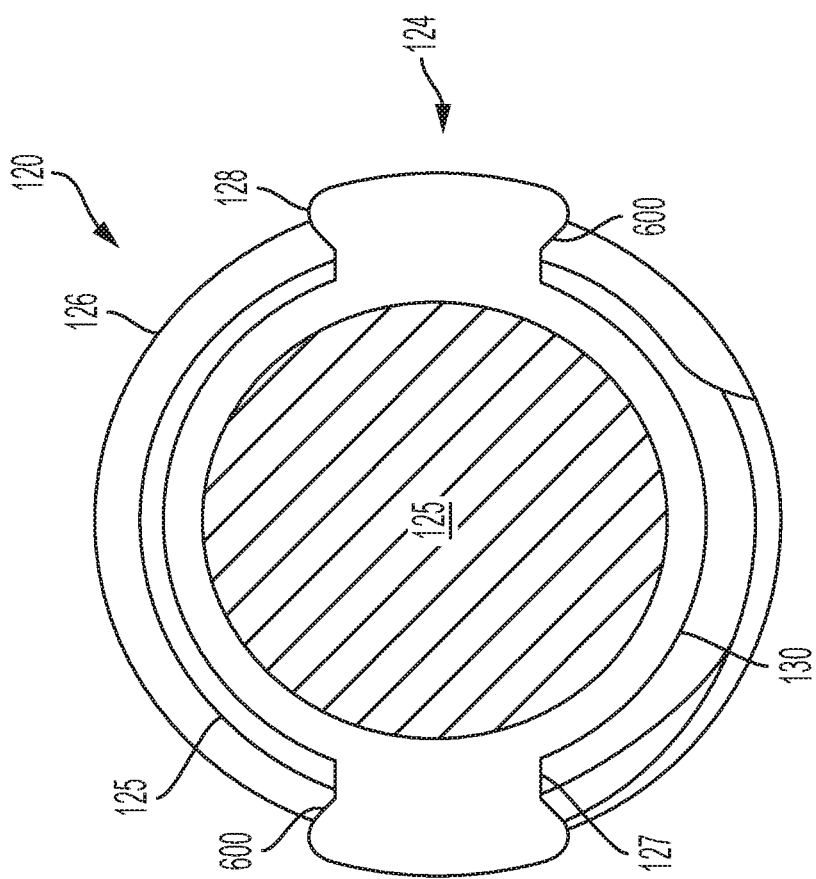
FIG. 9 is a cross section of the anti-splaying system, assembled, taken along line F9-F9 of FIG. 1.

FIG. 6 is a bottom view of the anti-splay set screw 120. Relative rotatability between the set screw body 125 and the locking component 124 is indicated by arrow in FIG. 6, as in FIG. 1.

The ends 128 of the locking component 124 are configured such that, when engaged with the arms 112 of the receiver 110, being slid into the anti-splay channels 118, keep the arms 112 from moving away from each other. The connection keeps each arm 112 from moving away from the other arm—i.e., keeps the arms 118 from splaying.

The ends 128 of the locking component 124 include first engagement or locking features 600, such as shoulders. The shoulders 600, which may be referred to as external shoulders, engage second, corresponding, engagement or locking features 700 (FIG. 7) of the receiver 110. The shoulders 600 of the locking component 124 can be referred to as external shoulders, corresponding to internal shoulders 800 of the receiver 110.

The configuration of each end 128 can be referred to as a double-dovetail, corresponding to the opposing shoulders 600.

In contemplated embodiments (not shown in detail), the locking or engaging features are configured in any of a variety of other ways. The features may include the locking component 124 having at each end 128 opposing internal shoulders. In this case, the internal shoulders of the locking component 124 form a locking-component void, for engaging with opposing external shoulders of a protrusion extending from or on an inner surface of each arm 112 of the receiver 110, for instance. In this case, the locking component 124 is aligned so that the protrusion of the receiver 112 is received in the void of the locking component 124, as the internal shoulder of the locking component 124 is slid down along the external shoulder of the protrusion of the receiver arms 112.

Figure 7:
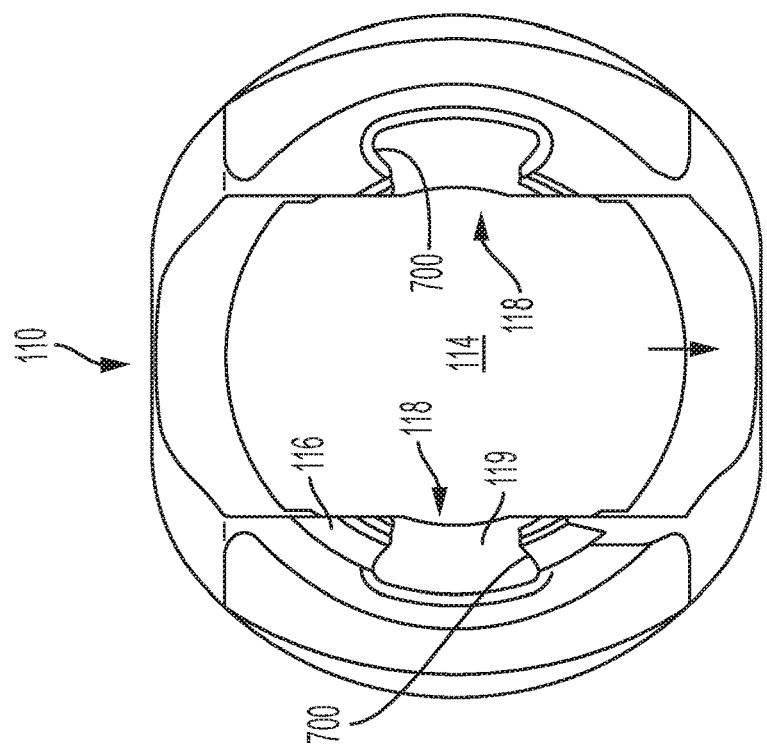
FIG. 7 is a top view of the anti-splay receiver.
Figure 8:
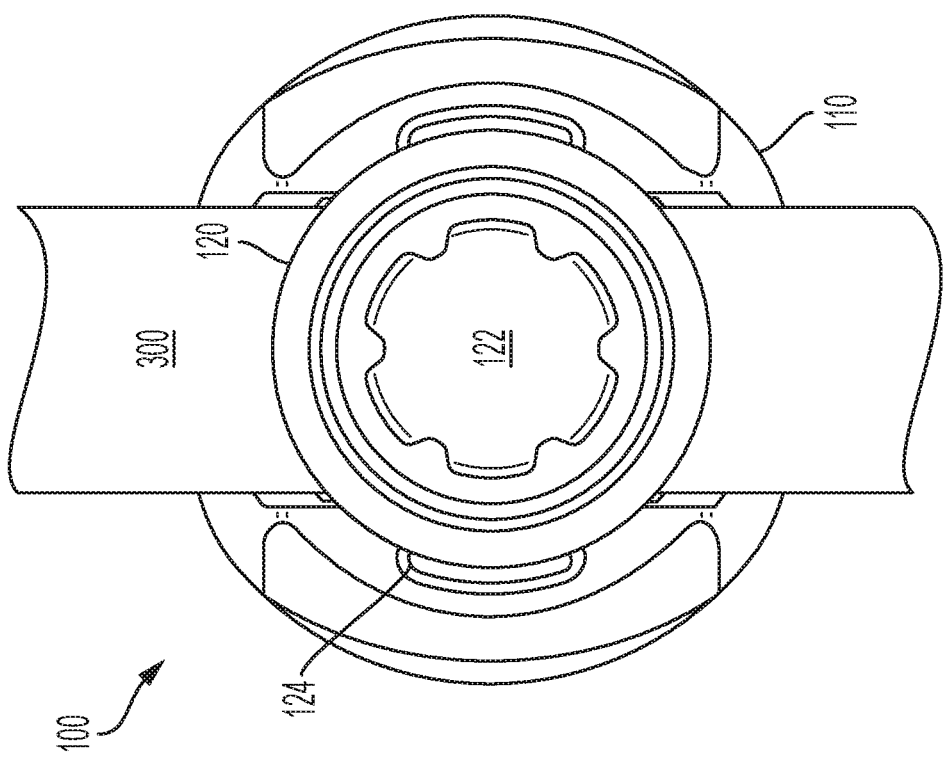
FIG. 8 is the top view of FIG. 7, with the anti-splay set screw inserted into the anti-splay receiver.

FIG. 7 illustrates a plan view of the anti-splay receiver 110. The view shows a top-down, or proximately looking, view of the receiver including anti-splay channels 118.

FIG. 8 is the top view of FIG. 7, with the anti-splay set screw 120 inserted into the anti-splay receiver 110, yielding the anti-splaying system 100 assembled. Full assembly in some embodiments includes the anti-splay set screw and receiver 120, 110 being connected to the bone anchor (not shown).

The rod 300 is shown seated in the anti-splay receiver 110. The rod 300 is secured in place there by the receiver 110 and the anti-splay set screw 120 threaded to the receiver 110, with the ends 128 of the locking component 124 secured in the anti-splay channel 118 of the receiver 110.

It should be understood that various aspects disclosed herein may be combined in combinations other than the combinations presented specifically in the description and the accompanying drawings. It should also be understood that, depending on the example, certain acts or events of any of the processes or methods described herein may be performed in other sequence, added, merged, or left out altogether (e.g., all described acts or events may not be necessary to carry out the techniques).

Any disclosure or claim herein referencing direction is not meant to limit interpretation of the disclosure, unless the disclosure or claim requires expressly such limitation. Reference, for instance, to movement up or down herein is not limited to movement in any certain direction during surgery or system assembly, as the surgery or assembly can be performed with any of a wide variety or orientations or in any suitable reference frame.

In addition, while certain aspects of this disclosure are described as being performed by a single module or unit for purposes of clarity, it should be understood that the techniques of this disclosure may be performed by a combination of units or modules associated with, for example, a medical device.

Unless defined specifically otherwise herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an," and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed:

1. An anti-splaying system comprising:
a receiver having a base, a first arm, a second arm, a first locking channel, and a second locking channel, the first arm and the second arm each extending from the base defining a rod-receiving cavity between the arms, the first and second arms including first and second inner threads formed in respective inner surfaces of the first and second arms, the first locking channel being formed in the inner surface of the first arm and extending from a proximal opening to a proximal bottom at or adjacent a first proximal beginning of the first inner thread, and the second locking channel being formed in the inner surface of the second arm and extending from a proximal opening to a proximal bottom at or adjacent a second proximal beginning of the second inner thread; and
a set screw having a driving portion, a body portion, external threads extending from the body portion, and an intermediate locking component connected rotatably to the body portion;

wherein the intermediate locking component of the set screw and the locking channels of the receiver are configured such that the intermediate locking component can, in operation of the system, be moved into a securing position in the locking channels and, when in the secured position, fixes the two arms from splaying away from each other.

2. The system of claim 1, wherein the intermediate locking component is connected rotatably to the body portion intermediate the driving portion and the external threads of the set screw.

3. The system of claim 1, wherein the intermediate locking component comprises opposing lateral ends sized and shaped corresponding to a size and shape of the locking channels, for mating engagement between the intermediate locking component and the locking channels.

4. The system of claim 3, wherein a first lateral end of the lateral ends comprises opposing shoulders sized and shaped to engage opposing shoulders of a first locking channel of the locking channels.

5. The system of claim 3, wherein the lateral ends include first and second lateral ends, and the intermediate locking component includes first and second arms connecting the first and second lateral ends respectively to the ring.

6. The system of claim 3, wherein the locking channels have a depth that is about twice as deep as the locking lateral ends are tall or less.

7. The system of claim 1, wherein the intermediate locking component includes a ring surrounding a portion of the set screw body.

8. The system of claim 7, wherein the body has a reduced diameter where the ring surrounds the body.

9. An anti-splaying system comprising:
a bone anchor;
a spinal rod;
a receiver being configured for connection with the bone anchor, the receiver having a base, a first arm, a second arm, a first locking channel, and a second locking channel, the first arm and the second arm each extending from the base defining a rod-receiving cavity between the arms, the first and second arms including first and second inner threads formed in respective inner surfaces of the first and second arms, the first locking channel being formed in the inner surface of the first arm and extending from a proximal opening to a proximal bottom at or adjacent a first proximal beginning of the first inner thread, and the second locking channel being formed in the inner surface of the second arm and extending from a proximal opening to a proximal bottom at or adjacent a second proximal beginning of the second inner thread; and
a set screw for securing a rod in place in the receiver in a portion of the system, the set screw having a driving portion, a body portion, external threads extending from the body portion, and an intermediate locking component connected rotatably to the body portion;
wherein the intermediate locking component of the set screw and the locking channels of the receiver are configured such that the locking component can, in operation of the system, be moved into a securing position in the locking channels and, when in the secured position, fixes the two arms from splaying away from each other.

10. The system of claim 9, wherein the intermediate locking component is connected rotatably to the body portion intermediate the driving portion and the external threads of the set screw.

11. The system of claim 9, wherein the intermediate locking component comprises opposing lateral ends sized and shaped corresponding to a size and shape of the locking channels, for mating engagement between the locking component and the locking channels.

12. The system of claim 11, wherein a first lateral end of the lateral ends comprises opposing shoulders sized and shaped to engage opposing shoulders of a first locking channel of the locking channels.

13. The system of claim 11, wherein the lateral ends include first and second lateral ends, and the intermediate locking component includes first and second arms connecting the first and second lateral ends respectively to the ring.

14. The system of claim 11, wherein the locking channels have a depth that is about twice as deep as the lateral ends are tall or less.

15. The system of claim 9, wherein the intermediate locking component includes a ring surrounding a portion of the set screw body.

16. The system of claim 15, wherein the body has a reduced diameter where the ring surrounds the body.

17. A method for making an anti-splaying system comprising:
forming a receiver configured for connection with a bone anchor, the receiver having a base, a first arm, a second arm, a first locking channel, and a second locking channel, the first arm and the second arm each extending from the base defining a rod-receiving cavity between the arms, the first and second arms including first and second inner threads formed in respective inner surfaces of the first and second arms, the first locking channel being formed in the inner surface of the first arm and extending from a proximal opening to a proximal bottom at or adjacent a first proximal beginning of the first inner thread, and the second locking channel being formed in the inner surface of the second arm and extending from a proximal opening to a proximal bottom at or adjacent a second proximal beginning of the second inner thread; and
presenting a set screw for securing a rod in place in the receiver in portion of the system, the set screw having a driving portion, a body portion, external threads extending from the body portion, and an intermediate locking component connected rotatably to the body portion and having opposing locking ends,
wherein the intermediate locking component of the set screw and the locking channels of the receiver are configured such that the locking component can, in operation of the system, be moved into a securing position in the locking channels and, when in the secured position, fixes the two arms from splaying away from each other.

18. The method of claim 17, wherein the intermediate locking component comprises a central ring connected to the locking ends.

19. A method of forming an anti-splaying system comprising:
presenting a set screw for securing the rod in place in a receiver in a portion of the system, the set screw having a driving portion, a body portion, external threads extending from the body portion, and an intermediate locking component connected rotatably to the body portion and having opposing locking ends,
wherein the intermediate locking component comprises a central ring and opposing lateral ends connected to the ring, the ring surrounding part of the body portion up to the driving portion.

20. The method of claim 19, wherein the part of the body portion is an outer surface of the body portion.

* * * * *